United States Patent [19]
Johnson

[11] Patent Number: 5,687,742
[45] Date of Patent: Nov. 18, 1997

[54] KNEE EXTENSION DEVICE

[76] Inventor: Lanny L. Johnson, 4528 Hagadorn, East Lansing, Mich. 48823

[21] Appl. No.: 551,233

[22] Filed: Oct. 31, 1995

Related U.S. Application Data

[63] Continuation of Ser. No. 79,731, Jun. 22, 1993, abandoned.

[51] Int. Cl.$^6$ ............................................. A61F 5/00
[52] U.S. Cl. ..................... 128/845; 602/35; 606/240; 482/907; 5/650
[58] Field of Search ......................... 602/5, 23, 24, 602/26, 35; 606/237, 240–241; 128/845, 846, 869, 870, 877–879, 882; 5/624, 648, 650, 651; 482/907, 142, 140

[56] References Cited

U.S. PATENT DOCUMENTS

| | | | |
|---|---|---|---|
| 3,498,605 | 3/1970 | Buttner | 482/142 |
| 3,639,927 | 2/1972 | Munch | 5/651 X |
| 3,931,654 | 1/1976 | Spann | 5/650 |
| 4,627,423 | 12/1986 | Kampner | 602/35 |
| 4,777,678 | 10/1988 | Moore | 606/240 X |
| 4,805,605 | 2/1989 | Glassman | 602/24 |
| 4,905,330 | 3/1990 | Jacobs | 5/648 X |
| 5,040,546 | 8/1991 | Deluhery | 128/870 X |
| 5,046,487 | 9/1991 | Scott | 5/650 X |

OTHER PUBLICATIONS

Instrument Makar Product Information Catalogue, 1992.

*Primary Examiner*—Linda C. Dvorak
*Attorney, Agent, or Firm*—Cushman Darby & Cushman, IP Group of Pillsbury Madison & Sutro LLP

[57] ABSTRACT

A knee extension device and method for using same for rehabilitating an injured knee by gradually extending the knee into a straightened position is disclosed. The knee extension device includes an elongated body member, a lower leg support member attached to the body member, and pressure applying strap capable of being wrapped around the body member. A leg is positioned on the body member with the lower portion of the leg resting on the support member. Pressure is selectively applied to the leg using the pressure applying strap to gradually force the knee towards a straightened position.

9 Claims, 2 Drawing Sheets

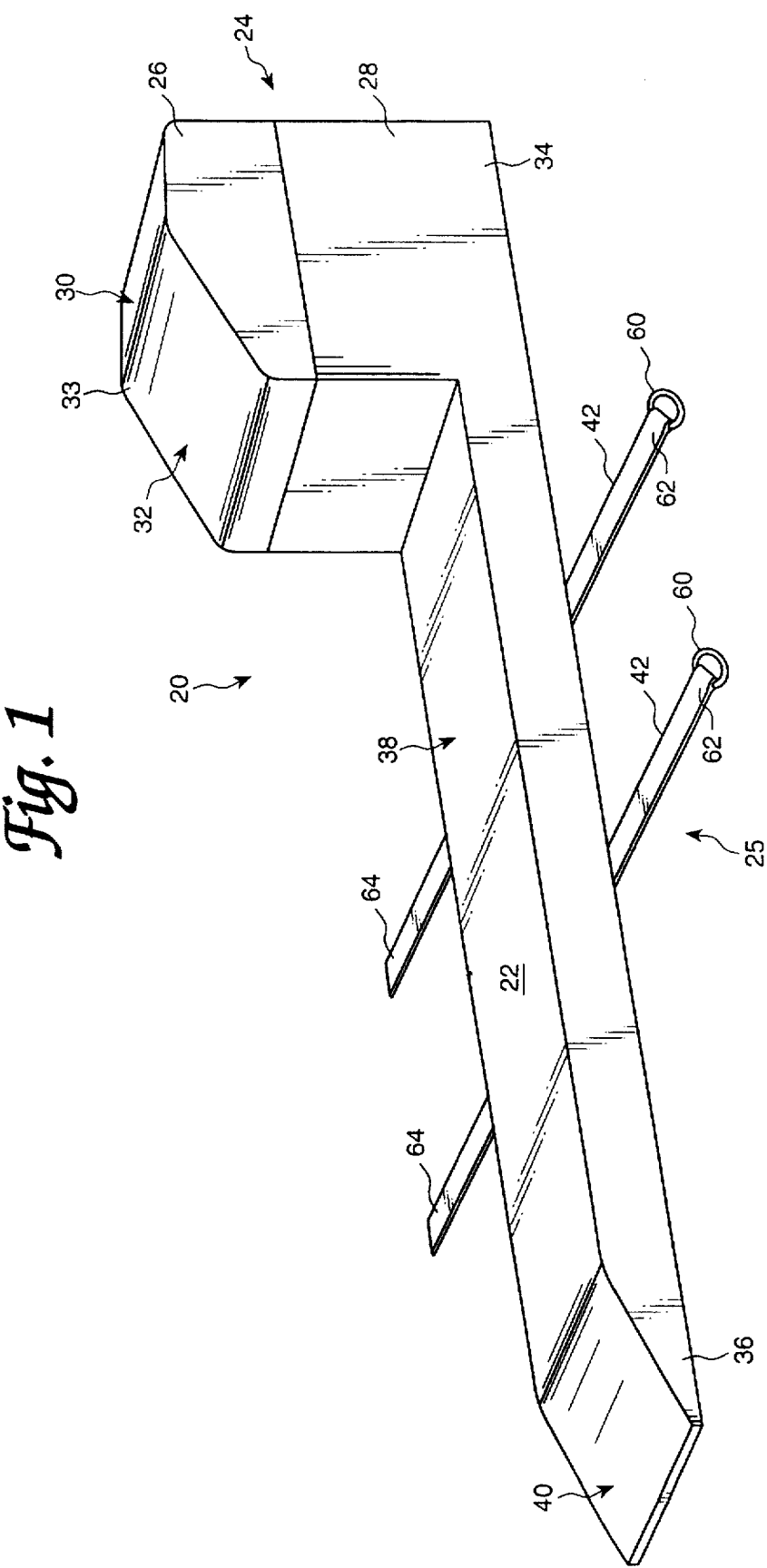

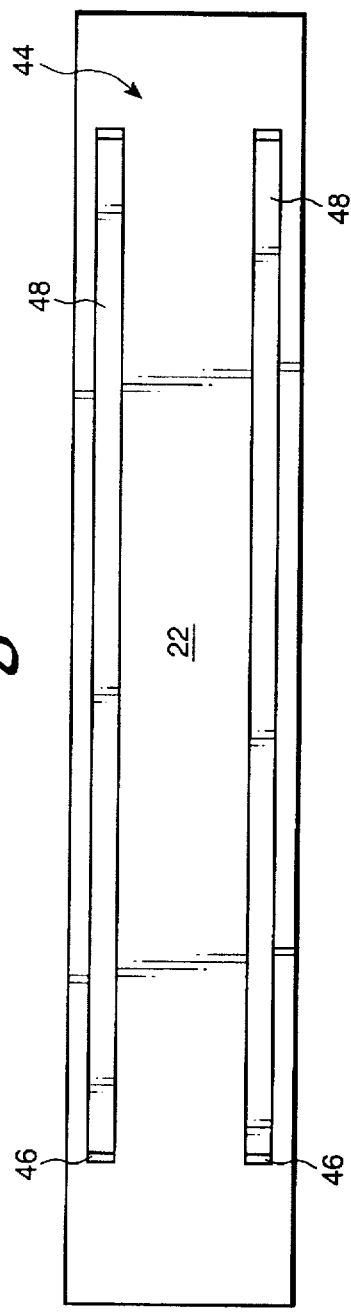
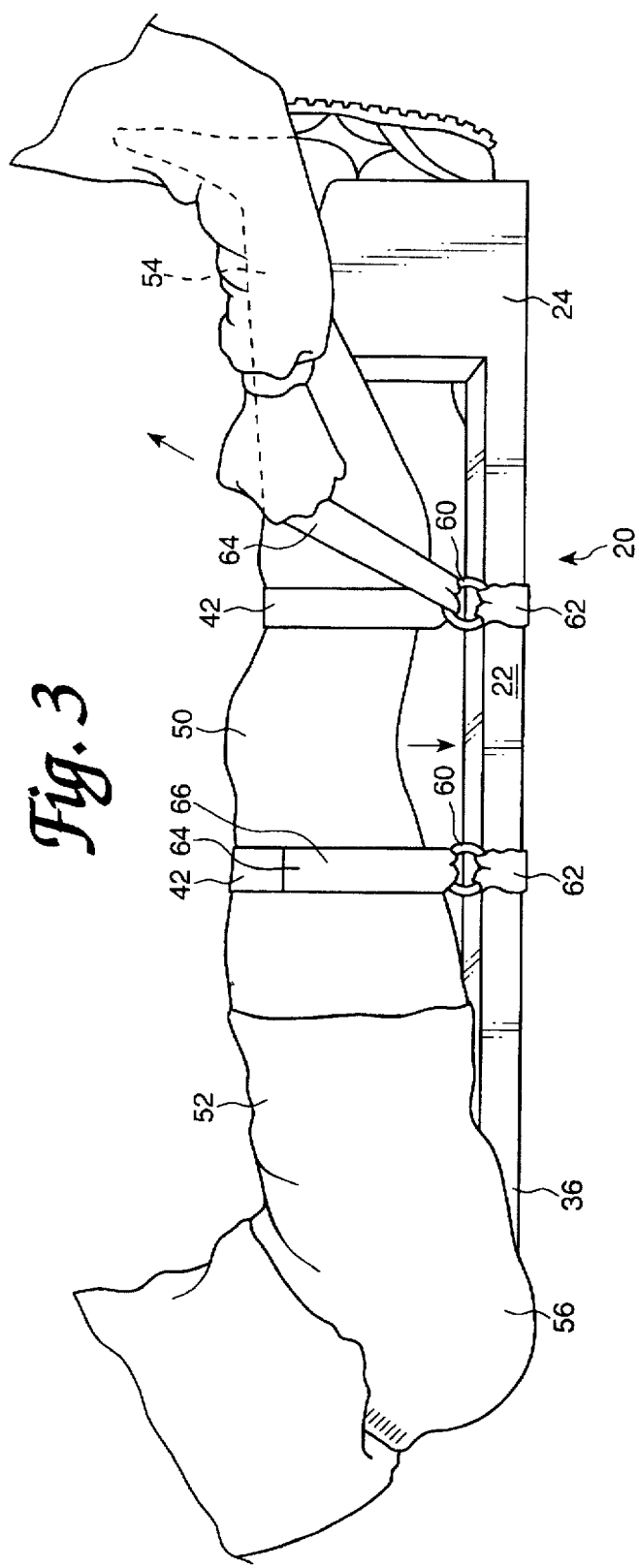

KNEE EXTENSION DEVICE

This is a continuation of application Ser. No. 08/079,731, filed on Jun. 22, 1993, which was abandoned upon the filing hereof.

BACKGROUND OF THE INVENTION

1. Field of the Invention

The present invention relates to a knee extension device for gradually straightening a knee during rehabilitation and a method for using same.

2. Description of a Related Art

After suffering a knee injury or knee surgery, it is common for a patient to have difficulty fully extending the knee. To rehabilitate the knee it is important that passive extension of the knee (i.e. the extension of the knee without assistance) be gradually increased so that the knee is capable of returning to its normal fully-extended position.

Various methods are known to increase passive extension of the knee. For example, it is known to place the knee in a cast. Periodically the cast is changed and, in doing so, the knee is gradually straightened. A cast, however, has obvious disadvantages in that it is bulky, expensive, and requires repeated visits to a medical facility. It also is known to have the patient undergo physical therapy, during which a therapist applies pressure to the knee to slowly increase the passive extension of the knee. As with the use of a cast, this method requires repeated visits to a medical professional (a therapist) and cannot be performed alone. Additionally, mechanical devices are known which the patient wears for extended periods during the day and/or night. Such devices typically are adjustable to permit gradual straightening of the knee over a period of time. These devices, however, are not easily secured to the knee. As a result, patients tend to cease using them before the knee has been fully rehabilitated.

SUMMARY OF THE INVENTION

It is an object of the present invention to provide a knee extension device which overcomes the problems and shortcomings associated with the above-described methods and apparatuses. In accordance with the principles of the present invention, this objective is achieved by providing a knee extension device and method for using the device which enables the knee to be gradually extended to a straightened position. The knee extension device includes an elongated body member, a lower leg support member attached to one end of the body member, and pressure applying means associated with the body member for applying a downward force on the knee. The lower leg support member provides an elevated surface above the upper surface of the elongated body member and serves to receive the lower portion of a patient's leg. The lower leg support, together with the body member, form a generally "L"-shaped structure. The pressure applying means is wrapped around the body member and the knee area which is positioned above the body member. When the pressure applying means is gradually and selectively tightened, the knee is urged toward a straightened position.

It is a further object of the present invention to provide a knee extension device which is simple in construction, economical to manufacture, easy to be used by and explained to, a patient, and effective in operation so that the patient will continue to use the device until the knee is fully rehabilitated.

These and other objects of the present invention will become more apparent during the course of the following detailed description of the invention and in the appended claims.

The invention may best be understood with reference to the accompanying drawings wherein an illustrative embodiment of the present invention is shown.

BRIEF DESCRIPTION OF THE DRAWINGS

FIG. 1 is a perspective view of a knee extension device according to the present invention;

FIG. 2 is a bottom view of the knee extension device shown in FIG. 1; and

FIG. 3 is a side elevational view of the knee extension device of FIG. 1 showing the operation of the device in gradually straightening a patient's knee.

DETAILED DESCRIPTION OF THE PREFERRED EXEMPLARY EMBODIMENT

Referring now more particularly to FIG. 1 of the drawings, there is shown therein a knee extension device, generally indicated at 20. The device 20 consists of an elongated body member 22, a lower leg support member, generally indicated at 24, attached to the body member 22 at one end thereof, and pressure applying means, generally indicated at 25, adapted to be wrapped around the body member 22 and a leg positioned thereon for applying a force on the knee urging it toward the body member 22.

The lower leg support member 24, disposed at a first end portion 34 of the body member 22, includes an upper portion 26 and a lower portion 28. In an exemplary embodiment of the present invention, the upper portion 26 includes first and second angularly related surfaces 30 and 32, each of which is disposed at an angle with respect to the upper surface 38 of the body member 22 and define an apex 33 therebetween. As shown, surfaces 30 and 32 slope in opposite directions from the apex 33 relative to the length of the body member 22. The body member 22 and the lower leg support 24 together form a generally upwardly facing "L"-shaped member.

The body member 22 includes, in addition to first end portion 34 and upper surface 38, a second end portion 36, and a lower surface 44 (FIG. 2). The surfaces 38 and 44 are located in parallel planes. An inclined upper surface 40 is provided at the second end portion 36 so that the second end portion 36 tapers toward the lower surface of the body member 22.

The upper portion 26 of the lower leg support member 24 is made of a soft material to enable the lower portion of a leg to comfortably rest thereon. In an exemplary embodiment, the lower portion 28 of the lower leg support member 24 is formed integrally with the body member 22, and both are formed from a foam-cushion material. As shown in FIG. 2, the body member 22, also preferably formed of foam, includes a pair of channels 46 provided in the lower surface 44. A pair of rigid wooden braces 48 within respective channels 46 maintain the body member 22 rigid.

The pressure applying means 25 comprises a pair of adjustable straps 42 adapted to be wrapped around the body member 22 and a leg positioned thereon. The straps each include a circular ring 60 at a first end 62 thereof into which the second strap end 64 is threaded. The straps are selectively tightened by pulling on the second end portion 64, and securing portion 64 to an intermediate portion of the strap 42 between the first and second ends 62 and 64. In the exemplary embodiment, the straps 42 are secured in a tightened position by "VELCRO" fastening devices (not shown). However, it is to be understood that any conventional means such as, snaps, clasps or buckles can be employed.

FIG. 3 illustrates how the knee extension device 20 is used to straighten a knee 50. The device 20 is placed on a generally flat surface, and the patient's leg 52 is placed over the body member 22 such that the lower portion of the leg 54 is seated on the lower leg support member 24, and the upper portion of the leg 56 is positioned on the angled exterior surface 40 (not shown in FIG. 3) of the second end portion 36 of the body member 22. The adjustable straps 42 are wrapped around the body member 22 and leg 52 above and below the knee 50. The second ends 64 of the straps are threaded through the respective rings 60. The straps 42 are gradually tightened by pulling on the second end portions 64, which can be done by the patient or by an assistant. Tightening of the straps 42 applies a force on opposite sides of the knee 50 thus urging the knee 50 toward a straightened position. As the straps 42 are tightened, the lower leg support 24 and the angled exterior surface 40 support the lower and upper portions 54 and 56 of the leg 52. The middle portion of the leg 52, including the knee 50, are forced toward the body member 22 into the gap formed by the upwardly facing "L" shape of the extension device 20. The straps 42 are maintained in a tightened position by selectively securing the second end portions 64 to intermediate portions thereof using, for example, "VELCRO" fastening devices. A strap 42 that is maintained in a tightened position is illustrated by strap 66 in FIG. 3. This tightening procedure can be easily and repeatedly performed by the patient or by an assistant to increase passive extension in the injured knee.

It will thus be seen that the objects of this invention have been fully and effectively accomplished. It will thus be realized, however, that the foregoing preferred specific embodiment has been shown and described for the purpose of this invention and is subject to change without departure from such principles. Therefore, this invention includes all modifications encompassed within the spirit and scope of the following claims.

What is claimed:

1. A knee extension device for enabling a knee to be gradually extended toward a straightened position, said knee extension device comprising:
    a substantially L-shaped elongated body member having an upper surface, a lower surface, a first end portion, a second end portion, and an upwardly projecting lower leg support member which is provided at said first end portion, said lower leg support member including:
        means for supporting an ankle region of a leg when said leg is positioned to overlie said elongated body member, said supporting means including angularly related first and second upper surfaces each disposed at an angle with respect to said lower surface of the body member and defining an apex therebetween, said angularly related first and second surfaces sloping in opposite directions from said apex;
    said L-shaped elongated body member defining a cavity under a knee region of said leg when said ankle region is supported by said supporting means, said cavity being large enough to permit substantial movement of said knee region of said leg into said cavity when a force is applied to an upper surface of said leg; and
    pressure applying means adapted to be wrapped around a portion of said leg and operatively related to said body member for selectively displacing said leg so that said knee region advances within said cavity, thereby moving said leg into a straightened position.

2. A knee extension device as defined in claim 1, wherein said upper surface of said elongated body member is substantially parallel to said lower surface.

3. A knee extension device as defined in claim 2, wherein said body member includes an inclined upper surface at said second end portion, said inclined surface defining a tapered configuration at said second end portion of the body member.

4. A knee extension device as defined in claim 1, wherein said supporting means of said lower leg support member is made of a soft material.

5. A knee extension device as defined in claim 4, wherein said body member is made of a foam cushion material and includes a rigid support structure therein.

6. A knee extension device as defined in claim 5, wherein said lower leg support member comprise a foam cushion formed integrally with said elongated body member.

7. A knee extension device as defined in claim 1, wherein said lower leg support member comprises a foam cushion formed integrally with said elongated body member.

8. A knee extension device for enabling a knee to be gradually extended toward a straightened position, said knee extension device comprising:
    a substantially L-shaped elongated body member having an upper surface, a lower surface, a first end portion, a second end portion, and an upwardly projecting lower leg support member provided at said first end portion, said body member being made of a foam cushion material and including a rigid support structure comprising a pair of channels in the lower surface of the body member extending the length thereof and within which a pair of braces are disposed, said lower leg support member including:
        means for supporting an ankle region of a leg when said leg is positioned to overlie said elongated body member, said supporting means being made of a soft material and having at least one upper surface disposed at an angle with respect to said lower surface of said body member;
    said L-shaped elongated body member defining a cavity under a knee region of said leg when said ankle region is supported by said supporting means, said cavity being large enough to permit substantial movement of said knee region of said leg into said cavity when a force is applied to an upper surface of said leg; and
    pressure applying means adapted to be wrapped around a portion of said leg and operatively related to said body member for selectively displacing said leg so that said knee region advances within said cavity, thereby moving said leg into a straightened position.

9. A knee extension device as defined in claim 8, wherein said lower leg support member comprises a foam cushion formed integrally with said elongated body member.

* * * * *